United States Patent
Berenguer Maimo

(10) Patent No.: US 6,723,852 B2
(45) Date of Patent: Apr. 20, 2004

(54) METHOD FOR OBTAINING DERIVATIVES OF [[(PYRIDIL SUBSTITUTED)METHYL]THIO]BENZOMIDAZOL

(75) Inventor: Ramon Berenguer Maimo, Barcelona (ES)

(73) Assignee: Esteve Quimica, S.A. (ES)

( * ) Notice: Subject to any disclaimer, the term of this patent is extended or adjusted under 35 U.S.C. 154(b) by 0 days.

(21) Appl. No.: 10/204,604

(22) PCT Filed: Apr. 10, 2001

(86) PCT No.: PCT/ES01/00143

§ 371 (c)(1),
(2), (4) Date: Aug. 20, 2002

(87) PCT Pub. No.: WO01/79194

PCT Pub. Date: Oct. 25, 2001

(65) Prior Publication Data

US 2003/0036656 A1 Feb. 20, 2003

(30) Foreign Application Priority Data

Apr. 14, 2000 (ES) .......... 200000989

(51) Int. Cl.[7] ............... C07D 401/12; A61K 31/4439
(52) U.S. Cl. ............... 546/273.4; 546/273.4; 546/273.7; 514/339
(58) Field of Search ............... 546/273.7, 273.4; 514/339

(56) References Cited

U.S. PATENT DOCUMENTS 4,628,098 A 12/1986 Nohara et al. ............ 546/271

FOREIGN PATENT DOCUMENTS

| EP | 0103553 | 3/1984 | |
| --- | --- | --- | --- |
| EP | 0729957 | 9/1996 | |
| ES | 2003658 | 11/1988 | |
| ES | 2024357 | * 2/1992 | ........ C07D/213/68 |
| ES | 2026761 | 5/1992 | |

OTHER PUBLICATIONS

C. Fontenas, et al., "The Boekelheide Reaction: Trifluoroacetic Anhydride as A Convenient Acylating Agent", *Synthetic Communications*, vol. 25, No. 5, 1995, pp. 629–633.

* cited by examiner

*Primary Examiner*—Alan L. Rotman
*Assistant Examiner*—Janet L Coppins
(74) *Attorney, Agent, or Firm*—Ostrolenk, Faber, Gerb & Soffen, LLP

(57) ABSTRACT

The method for obtaining derivatives of [[(pyridil substituted)methyl]thio]benzomidazol (I), where each of $R_1$, $R_3$ and $R_4$, independently of each other, is hydrogen, an alkyl, alkoxy or fluorinated alkoxy of 1 to 6 carbon atoms, and $R_2$ is nitro, halogen, alkoxy or halogenated alkoxy of 1 to 6 carbon atoms, or a group $—OR—(CH_2)_n—OR_8$, where n is an integer between 1 and 6 and $R_8$ represents hydrogen or an alkyl group with 1 to 6 carbon atoms, which involves (a) reacting an N-oxide of a methylpyridine with an anhydride of activated carboxylic acid or of sulfonic acid, and (b) reacting the intermediate formed in stage (a) with a corresponding mercaptobenzomidazol. The compounds (I) are useful in the synthesis of derivatives of [[(pyridil substituted)methyl]sulfinyl]benzomidazol, such as omeprazol, lansoprazol, rabeprazol or pantoprazol.

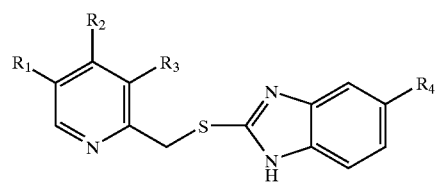

(I)

22 Claims, No Drawings

METHOD FOR OBTAINING DERIVATIVES OF [[(PYRIDIL SUBSTITUTED)METHYL]THIO]BENZOMIDAZOL

FIELD OF THE INVENTION

This invention relates to the preparation of derivatives of [[(pyridil substituted)methyl]thio]benzomidazol useful as intermediates in the synthesis of derivatives of [[(pyridil substituted)methyl]sulfinyl]benzomidazol.

BACKGROUND OF THE INVENTION

Certain derivatives of [[(pyridil substituted)methyl]sulfinyl]benzomidazol, among which are omeprazol, 2-[[3,5-dimethyl-4-methoxy-2-pyridil)methyl]sulfinyl]-5-methoxy-1H-benzomidazol, lansoprazol, 2-[[[3-methyl-4-(2,2,2-trifluoroethoxy)-2-pyridil]methyl]sulfinyl]-1H-benzomidazol, rabeprazol, 2-[[[3-methyl-4-(3-methoxypropoxy)-2-pyridil]methyl]sulfinyl]-1H-benzomidazol, and pantoprazol, 5-difluoromethoxy-2-[[(3,4-dimethoxy-2-pyridil)methyl]sulfinyl]-1H-benzomidazol, are anti-ulcerous agents useful in the treatment of stomach and duodenal ulcers, Zollinger-Ellison syndrome and reflux oesophagitis.

One of the key intermediates in the synthesis of said compounds is the derivative of [[(pyridil substituted)methyl]thio]benzimidazole, with the general formula (I)

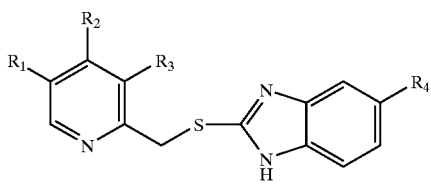

where each of $R_1$, $R_3$ and $R_4$, independently of each other is hydrogen, an alkyl group with 1 to 6 carbon atoms, an alkoxy group with 1 to 6 carbon atoms, or a fluorinated alkoxy group with 1 to 6 carbon atoms, and $R_2$ is a nitro group, a halogen, an alkoxy group with 1 to 6 carbon atoms, a halogenated alkoxy group with 1 to 6 carbon atoms, or a group —O—$(CH_2)_n$—$OR_8$, where n is an integer between 1 and 6, both inclusive, and $R_8$ represents hydrogen or an alkyl group with 1 to 6 carbon atoms.

Although many methods have been described for obtaining said compounds with the formula (I), one of the most widely used in the one based on coupling a derivative of 2-methylpyridine (II)

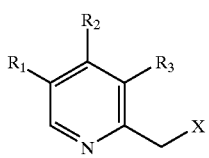

with the corresponding mercaptobenzomidazol (III):

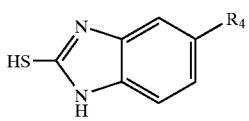

The literature describes compounds with the formula (II), where X is a halogen, as the intermediates usually chosen to perform this reaction.

The synthesis of compounds with the formula (II) can be effected by several methods, such as:

by a radical halogenation of the corresponding methylpyridine [ES 2036948] using as a chlorination reagent trichloroisocyanuric acid, N-chlorosuccinimide, etc.;

from the suitable hydroximethylpyridine, by substitution of the hydroxyl by a halogen [ES 2036948, EP 174726, ES 2036502] using as reagent for example thyonil chloride;

from the N-oxide of the corresponding 2-methylpyridine, compound with formula (IV)

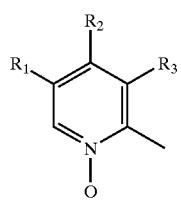

Where $R_1$ is hydrogen, $R_2$ is nitro and $R_3$ is methyl, using as a reagent an alkyl or arylsulfonyl chloride, or a carboxylic acid chloride [ES 2060541]; or based on the N-oxide of the corresponding 2-methylpyridine, compound with the formula (IV), in two stages, using trichloroisocyanuric acid and later addition of sulfur chloride [ES 2036948].

All of the above methods suffer from important drawbacks:

in general, they require a large number of stages, and in some cases they use very irritating reagents, such as acid chlorides that form hydrochloric acid in the process;

the use of derivatives of 2-halomethylpyridines (compound with the formula (II) where X is a halogen), which usually bring about high levels of irritation, such as the derivatives 4-nitro and 4-(2,2,2-trifluoroethoxy) of 2-chloromethyl-3-methylpyridine and 2-chloromethyl-3,5-dimethyl-4-methoxypyridine; and in the case of the compound with the formula (IV) where $R_2$ is a nitro group, during the preparation of the compounds with formulae (I) and (II) byproducts are formed in which $R_2$ is a halogen, mainly chlorine (as this is the most used derivative), which in the case of low activated pyridines are quite unreactive to nucleophilic substitution in this position. For example, this is the case with omeprazol, where these byproducts are impurities that are difficult to eliminate.

SUMMARY OF THE INVENTION

The invention deals with the problem of developing an alternative method of synthesis of derivatives of [[(pyridil substituted)methyl]thio]benzomidazol, with the general formula (I), which are useful as intermediates of derivatives of [[(pyridil substituted)methyl]sulfinyl]benzomidazol.

The solution disclosed by this invention consists of a process with two stages performed consecutively, and optionally in the same reaction medium, comprising the reaction of the corresponding N-oxide of methylpyridine with the anhydride of activated carboxylic acid or sulfonic acid, and the reaction of the intermediate formed with the corresponding mercaptobenzomidazol.

The method disclosed by this invention has the competitive advantage that it significantly reduces the number of synthesis stages, which implies a great increase of industrial interest as it reduces the cost in comparison with most methods described and reduces the levels of residues formed.

In addition, the intermediates formed after reaction of the corresponding N-oxide of methylpyridine with the activated carboxylic acid or sulfonic acid anhydride produce much lower levels, or nearly inexistent levels, of irritation as compared to the compounds of formula (II), where X is a halogen. Furthermore, the method provided by the invention avoids the handling of these intermediates as they can be made to react in the reaction medium itself.

A further competitive advantage is that the formation is prevented of the corresponding derivative 4-chloro of 2-chloromethylpyridine, which is an important impurity in certain cases, such as in the synthesis of omeprazol.

One object of this invention is a method for obtaining derivatives of [[(pyridil substituted)methyl]thio] benzomidazol, with the general formula (I).

A further object of this invention is a method for obtaining derivatives of [[(pyridil substituted)methyl]sulfinyl] benzomidazol, from compounds with the general formula (I) obtained by the method provided in this invention.

An additional object of this invention are intermediates formed by the reaction of the corresponding N-oxide of methylpyridine with the activated carboxylic acid anhydride of sulfonic acid anhydride, useful as intermediates in the synthesis of derivatives of [[(pyridil substituted)methyl] thio]benzomidazol with the general formula (I). The method for obtaining said intermediates is a further object of this invention.

DETAILED DESCRIPTION OF THE INVENTION

The invention provides a method, hereinafter referred to as the method of the invention, for obtaining derivatives of [[(pyridil substituted)methyl]thio]benzomidazol, with the general formula (I)

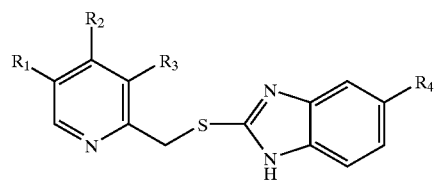

(I)

where
each one of $R_1$, $R_3$ and $R_4$, independently of each other, is hydrogen, an alkyl group with 1 to 6 carbon atoms, an alkoxy group with 1 to 6 carbon atoms, or a fluorinated alkoxy group with 1 to 6 carbon atoms, and $R_2$ is a nitro group, a halogen, preferably chlorine, an alkoxy group with 1 to 6 carbon atoms, a halogenated alkoxy group, preferably fluorine or chlorine, with 1 to 6 carbon atoms, or a group —O—$(CH_2)_n$—$OR_8$, where n is an integer between 1 and 6, both inclusive, and $R_8$ represents hydrogen or an alkyl group with 1 to 6 carbon atoms,
which comprises:
a) reacting an N-oxide of methylpyridine with the general formula (IV)

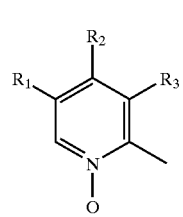

(IV)

and where $R_1$, $R_2$ and $R_3$ are as described previously; with (i) an anhydride of activated carboxylic acid with the general formula $(R_6CO)_2O$, where $R_6$ is a halogenated alkyl group, or (ii) with an anhydride of sulfonic acid with the general formula $(R_7SO_2)_2O$, where $R_7$ is an alkyl group, a halogenated alkyl group or an aryl group, optionally substituted with an alkyl group, in an organic solvent, to provide an intermediate with the general formula (V) or the corresponding salt

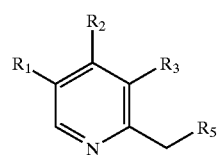

(V)

where
$R_1$, $R_2$ and $R_3$ are as described previously, and
$R_5$ is $OCOR_6$ or $OSO_2R_7$, where $R_6$ and $R_7$ are as described previously; and
b) reacting said intermediate compound with the general formula (V) with a derivative of 2-mercaptobenzomidazol with the general formula (III)

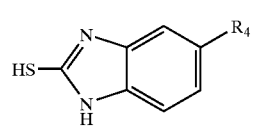

(III)

where $R_4$ is as defined above,
in the presence of a base in an organic solvent, to give the compound with the general formula (I).

In the sense meant in this description, the term "fluorinated alkoxy group with 1 to 6 carbon atoms" means an alkoxy group with 1 to 6 carbon atoms containing one or more fluorine atoms in substitution of one or more hydrogen atoms, such as 2,2,2-trifluoroethoxy or difluoromethoxy. Likewise, a "halogenated alkoxy group with 1 to 6 carbon atoms" means an alkoxy group with 1 to 6 carbon atoms containing one or more halogen atoms, preferably fluorine or chlorine, in substitution of on or more hydrogen atoms. Similarly, "halogenated alkyl group" means an alkyl group containing one or ore halogen atoms, preferably fluorine, in substitution of one or more hydrogen atoms.

Stage a) of the method of the invention occurs in an organic solvent, such as a chlorinated solvent or an ether, preferably dichloromethane, 1,2-dichloroethane, chloroform or 1,1,1-trichloroethane, at a temperature between 20° C. and 90° C., preferably between 60° C. and 84° C. In a particular realization the activated carboxylic acid anhydride is trifluoroacetic anhydride, while in another he sulfonic acid anhydride is methansulfonic anhydride or toluensulfonic anhydride.

The intermediate with the general formula (V), can be isolated if desired as a salt of the acid corresponding to the anhydride used in the reaction, or it can be made to react in the reaction medium with the derivate of 2-mercaptobenzomidazol (III).

Stage b) of the method of the invention occurs in an organic solvent, such as a chlorinated solvent, an ether or alcohol, preferably dichloromethane, 1,2-dichloroethane, chloroform, 1,1,1-trichloroethane or methanol, at a temperature between 10° C. and 40° C., in the presence of a base, preferably triethylamine or sodium methoxide. The compound with the general formula (I) obtained can be isolated if desired as a solid, precipitating it in water/alcohol, preferably in a short-chain alcohol or in water/acetone.

The compound with the general formula (I) is useful as an intermediate for the synthesis of derivares of [[(pyridil substituted)methyl]sulfinyl]benzomidazol, among which are compounds with therapeutic activity such as omeprazol, lansoprazol, rabeprazol and pantoprazol. For this the thioether group present in the compound with the general formula (I) is oxidized to a sulfoxide group by conventional means, such as with an oxidizing agent as hydrogen peroxide or sodium percarbonate in the presence of a molybdenum catalyst in a suitable solvent. If the starting point is a compound with the formula (I) where $R_2$ is a nitro group or a halogen, said nitro group or halogen is substituted by the corresponding alkoxy prior to performing the oxidation.

The preferred compounds with formula (I) are those in which $R_1$ is hydrogen or methyl, $R_2$ is nitro, chloro, methoxy, 2,2,2-trifluoroethoxy, 3-methoxypropoxy 3-hydroxypropoxy or 3-chloropropoxy, $R_3$ is methyl or methoxy, and $R_4$ is hydrogen, methoxy or difluoromethoxy.

The compounds with the formula (V) are an additional object of this invention. These compounds may be obtained by reacting the N-oxide of methylpyridine with the formula (IV) with an anhydride of activated carboxylic acid with the general formula $(R_6CO)_2O$ or with an anhydride of sulfonic acid with the general formula $(R_7SO_2)_2O$, where $R_6$ and $R_7$ are as described previously, and may be isolated if desired as a salt of the corresponding acid of the anhydride used in the reaction.

The compounds with formula (V) are useful as intermediates in the synthesis of derivatives of [[(pyridil substituted)methyl]thio]benzomidazol with the general formula (I).

In a specific realization the intermediate with the formula (V) is chosen among the group of compounds with formula (V) in which $R_1$ is hydrogen or methyl, $R_2$ is nitro, chloro, methoxy, 2,2,2-trifluoroethoxy, 3-methoxypropoxy, 3-hydroxypropoxy or 3-chloropropoxy, $R_3$ is methyl or methoxy, and $R_5$ is trifluoroacetyloxy, mesiloxy or tosiloxy. In a specific realization, the compound with the formula (V) is a compound with the formula (V) where $R_1$ is hydrogen, $R_2$ is nitro, $R_3$ is methyl and $R_5$ is trifluoroacetyloxy, mesiloxy or tosiloxy. In another realization, the compound with the formula (V) is a compound with the formula (V) where $R_1$ is methyl, $R_2$ is nitro, $R_3$ is methyl and $R_5$ is trifluoroacetyloxy, mesiloxy or tosiloxy. In another specific realization, the compound with the formula (V) is a compound with the formula (V) where $R_1$ is hydrogen, $R_2$ is nitro or chloro, $R_3$ is methoxy and $R_5$ is trifluoroacetyloxy, mesiloxy or tosiloxy.

The following examples are meant for purposes of illustration of the invention and are not meant as a definition of its limits.

EXAMPLE 1

2-[[(3-methyl-4-nitro-2-pyridil)methyl]thio]-1H-benzomidazol 10 g of N-oxide of 2,3-dimethyl-4-nitropyridine were dissolved in 50 ml of dichloromethane and 18.7 g of trifluoroacetic anhydride were added drop by drop. After the addition was finished it was heated at reflux for 4 hours. At the conclusion of the reaction, the excess anhydride was distilled and the necessary dichloromethane was added to obtain the same solvent relation as in the first stage. This was then cooled to ambient temperature and 12.9 g of triethylamine and 8.9 g of 2-mercaptobenzomidazol were added. This was kept at ambient temperature until the conclusion of the reaction. The solvent was evaporated and 50 ml of ethanol and 40 ml of water were added. This was stirred for 30 minutes and filtered, providing 7.8 g (43%) of the desired product.

EXAMPLE 2

2-[[(3-methyl-4-nitro-2-pyridil)methyl]thio]-1H-benzomidazol 10 g of N-oxide of 2,3-dimethyl-4-nitropyridine were dissolved in 100 ml of 1,2-dichloroethane and 15.5 g were added of methansulfonic anhydride. This was heated to 60-70° C. for 2 hours. Afterwards 4.5 g of triethylamine were added and kept at the same temperature until the end of the reaction. This was cooled to 25–30° C. and 13.5 g were added of triethylamine as well as 8.9 g of 2-mercaptobenzomidazol. This was kept at ambient temperature for 2–3 hours. At the end of the second stage the solvent was distilled at reduced pressure and 50 ml of ethanol and 38 ml of water were added. The pH was corrected to 10.5–11 using sodium hydroxide, and this was kept at ambient temperature for 1 hour. This was filtered and dried to provide 12.9 g (72%) of the desired product.

EXAMPLE 3

2-mesiloximethyl-3-methyl-4-nitropyridine methansulfonate 40 g of N-oxide of 2,3-dimethyl-4-nitropyridine were dissolved in 400 ml of chloroform and 82.9 g added of methansulfonic anhydride. After the addition finishes it was heated at reflux for 9 h. After conclusion of the reaction, it was cooled to 10° C. and the solid filtered. 76.4 g (94%) of the desired product were obtained.

EXAMPLE 4

2-[[(3-methyl-4-nitro-2-pyridil)methyl]thio]-1H-benzomidazol 20 g of 2-mesiloxymethyl-3-methyl-4-nitropyridine methansulfonate were suspended in 200 ml of chloroform and cooled to 5–10° C., then adding 13.3 g of triethylamine and 8.78 g of 2-mercapto-1H-benzomidazol. This was heated to 20° C. for 3 h and, at the end of the reaction, the solvent was evaporated at reduced pressure. To the residue were added 50 ml of ethanol and 37 ml of water and basified with 25% sodium hydroxide. This was filtered and dried to provide 14.4 g (82%) of the desired compound.

EXAMPLE 5
2-[[[3-methyl-4-(2,2,2-trifluoroethoxy)-2-pyridil]methyl]thio]-1H-benzomidazol 2.5 g of N-oxide of 2,3-dimethyl-4-(2,2,2-trifluoroethoxy)pyridine were dissolved in 25 ml of 1,2-dichloroethane and 4.1 g of methansulfonic anhydride were added. This was heated to reflux for 3 hours. It was cooled to ambient temperature, adding 3.73 g of triethylamine as well as 1.7 g of 2-mercaptobenzomidazol. This was kept at the same temperature until the end of the reaction. The solvent was eliminated at reduced pressure and the residue was crystallized with ethanol/water (1:1). 1.5 g (38%) of the desired product was obtained.

EXAMPLE 6
2-[[[3-methyl-4-(2,2,2-trifluoroethoxy)-2-pyridil]methyl]thio]-1H-benzomidazol 228 g of 2,2,2-trifluoroethanol were added on a mixture of 260 g of potassium carbonate and 342 ml of acetonitryl. Afterwards 114 g of [2-[[(3-methyl-4-nitro-2-pyridil)methyl]thio]-1H-benzomidazol] were loaded and this was heated to reflux for 12–15 hours. After conclusion of the reaction the suspension was filtered and the solvent evaporated at reduced pressure. 137 ml of acetone were added as well as 547 ml of water, heating at reflux for 1 hour. This was then cooled and filtered, providing 116 g (86%) of the desired compound.

EXAMPLE 7
2-[[[3-methyl-4-(2,2,2-trifluoroethoxy)-2-pyridil]methyl]sulfinyl]-1H-benzomidazol 10 g of 2-[[[3-methyl-4-(2,2,2-trifluoroethoxy)-2-pyridil]methyl]thio]-1H-benzomidazol were dissolved in 50 ml of methanol and 0.3 g of ammonium molybdate were added. The solution was cooled to 10° C. and 3.35 g of sodium percarbonate were slowly added, stirring at the same temperature for 15 hours. After conclusion of the reaction, 250 ml of water were added and the pH of the mixture adjusted to 10 with 10% acetic acid. This was stirred for 1 hour and the solid obtained was filtered, washed with water and dried in a vacuum oven at 60° C., providing 9.4 g of lansoprazol (90%).

EXAMPLE 8
2-[[(3,5-dimethyl-4-nitro-2-pyridil)methyl]thio]-5-methoxy-1H-benzomidazol 10 g of N-oxide of 2,3,5-trimethyl-4-nitropyridine were dissolved in 100 ml of 1,2-dichloroethane and 19.1 g of methansulfonic anhydride were added. This was heated to reflux for 6 hours. Afterwards, it was cooled to 15–20° C. and 22.3 g of triethylamine and 8.9 g of 2-mercapto-5-methoxybenzomidazol were added. This was kept at ambient temperature for 2–3 hours. At the end of the second stage the solvent was distilled at reduced pressure and 25 ml of methanol were added. This was heated to reflux and 25 ml of water added. This was then cooled to ambient temperature and maintained thus for 2 hours. It was then filtered and dried, to provide 14.7 g (78%) of the desired product.

EXAMPLE 9
2-[[(3,5-dimethyl-4-methoxy-2-pyridil)methyl]thio]-5-methoxy-1H-benzomidazol A solution was prepared of 24 g of sodium methoxide in 60 ml of methanol and added to the mixture of 1.25 g of triethylbenzolammonium chloride and 25 g of 2-[[(3,5-dimethyl-4-nitro-2-pyridil)methyl]thio]-5-methoxy-1H-benzomidazol in 40 ml of methanol. Afterwards this was heated to reflux for 6–10 hours. After conclusion of the reaction, water was added and the product extracted in the dichloromethane. The solvent was evaporated and 10.6 g (89%) of the desired compound were obtained.

EXAMPLE 10
2-mesiloximethyl-3,5-dimethyl-4-nitropyridine methanosulphate 50 g of N-oxide of 2,3,5-trimethyl-4-nitropyridine were dissolved in 250 ml of chloroform. 95.8 g of methansulfonic anhydride were added. This was heated to reflux for 4 h. After conclusion of the reaction, the solvent was evaporated at reduced pressure and 75 ml of isopropanol were added, it was cooled to 5° C. and the solid was filtered. 82.4 g (84%) of the desired product were obtained.

EXAMPLE 11
2-[[(3,5-dimethyl-4-methoxy-2-pyridil)methyl]thio]-5-methoxy-1H-benzomidazol 275 g of 2-mesiloxymethyl-3,5-dimethyl-4-nitropyridine methanosulfonate were suspended in a solution of 83 g of sodium methoxide in 1.37 l of methanol at −10° C. 139 g of 2-mercapto-5-methoxy-1H-benzomidazol were added. This was heated to 20° C. for 6 h, 250 g of sodium methoxide were added and set in reflux for 16 h. Water was added and extracted in dichloromethane. The organic solvent was eliminated at reduced pressure, providing an oil, which was dissolved in 468 ml of methanol yielding 648 g (92%) of the desired product in solution.

EXAMPLE 12
2-[[(3,5-dimethyl-4-methoxy-2-pyridil)methyl]sulfinyl]-5-methoxy-1H-benzomidazol 30g of 2-[[(3,5-dimethyl-4-methoxy-2-pyridil)methyl]thio]-5-methoxy-1H-benzomidazol were dissolved in 150 ml of methanol and 0.9 g of ammonium molybdate were added. This was cooled to 10° C. and 11.7 g of sodium percarbonate were added slowly. It was kept at this temperature for 15 hours, after which 450 ml of water were added slowly and the pH adjusted to 8.6 with 10% acetic acid. The solid obtained was washed with water and acetone. After drying in a vacuum oven at 30–35° C. 25.4 g of omeprazol (81%) were obtained.

EXAMPLE 13
2-mesiloximethyl-3-methoxy-4-nitropyridine methanosulphate 510 mg of N-oxide of 2-methyl-3-methoxy-4-nitropyridine were dissolved in 5 ml of chloroform. 625 mg were added of methansulfonic anhydride and heated to reflux for 6 h. It was evaporated to dryness at reduced pressure and 3 ml of isopropanol were added. It is cooled to −5° C. and the solid was filtered, providing 666 mg (67%) of the desired product.

EXAMPLE 14
5-difluoromethoxy-2-[[(3,4-dimethoxy-2-pyridil)methyl]thio]-1H-benzomidazol 2.0 g of 2-mesiloxymethyl-3-methoxy-4-nitropyridine methanosulfate were suspended in a solution of 0.60 g of sodium methoxide in 10 ml of methanol at 0° C. 1.2 g of 5-difluoromethoxy-2-mercapto-1H-benzomidazol were added and heated to 20° C. for 3 h, then adding 1.80 g of sodium methoxide and setting in reflux for 12 h. The residue was dissolved in water, and extracted with dichloromethane. Water was added and this was neutralized with acetic acid, then evaporating to dryness at reduced pressure to provide 1.82 g (67%) of the desired product.

EXAMPLE 15

4-chloro-2-mesiloximethyl-3-methoxypyridine methanosulphate 310 mg of N-oxide of 4-chloro-2-methyl-3-methoxypyridine were dissolved in 3.1 ml of chloroform. 625 mg of methansulfonic anhydride were added and heated to reflux for 17 h, evaporating to dryness at reduced pressure and adding 1 ml of isopropanol. This was cooled to −5° C. and the solid was filtered, providing 294 mg (47%) of the desired product.

EXAMPLE 16

2[[(4-chloro-3-methoxy-2-pyridil)methyl]thio]-5-difluoromethoxy-1H-benzomidazol 280 mg of 4-chloro-2-mesiloxymethyl-3-methoxypyridine methanosulfate were suspended in 1.5 ml of methanol and cooled to 0° C. 0.31 ml of triethylamine and 135 mg of 5-difluoromethoxy-2-mercapto-1H-benzomidazol were added. This was heated to 20° C. for 5 h, evaporating to dryness at reduced pressure. The residue was dissolved in chloroform and washed with 10% sodium bicarbonate and with 2% acetic acid. The organic phase was separated and the solvent was evaporated at reduced pressure, providing 253 mg (81%) of the desired product.

EXAMPLE 17

2[[(3,4-dimethoxy-2-pyridil)methyl]thio]-5-difluoromethoxy-1H-benzomidazol 200 mg of 2-[[(4-chloro-3-methoxy-2-pyridil)methyl]thio]-5-difluoromethoxy-1H-benzomidazol were dissolved in 1 ml of methanol and 224 mg of sodium methoxide were added. This was heated to reflux for 24 h. and cooled to 20° C., then adding 10 ml of chloroform and washing with 10% sodium bicarbonate and 2% acetic acid. The organic phase was separated and the solvent was evaporated at reduced pressure, providing 116 mg (61%) of the desired product.

EXAMPLE 18

5-difluoromethoxy-2-[[(3,4-dimethoxy-2-pyridil)methyl]sulfinyl]-1H-benzomidazol 310 mg of 5-difluoromethoxy-2-[[(3,4-dimethoxy-2-pyridil)methyl]thio]-1H-benzomidazol were dissolved in 1.5 ml of methanol and 12 mg of ammonium molybdate added. The solution was cooled to 5° C., adding 0.11 g of sodium percarbonate and keeping stirred at the same temperature for 4 h. After conclusion of the reaction 3 ml of water were added, then heated to 20° C. and adjusting the pH of the mixture to 7.5 with acetic acid. The mixture was extracted with 5 ml of dichloromethane and the organic phase separated and then washed with 10 ml of water. The solvent was evaporated at reduced pressure, providing 274 mg of pantoprazol (88%).

EXAMPLE 19

2[[[3-methyl-4-(3-methoxypropoxi)-2-pyridil]methyl]thio]-1H-benzomidazol 50.0 g of 2-[[(3-methyl-4-nitro-2-pyridil)methyl]thio]-1H-benzomidazol, 69.0 g of potassium carbonate were suspended in 150 ml of 3-methoxy-1-propanol and 50 ml of isopropanol. The mixture was heated to 85° C. for 48 h and cooled to 20° C. 1.5 l of chloroform were added and the suspension obtained was filtered. The chloroform waters were washed with water and the organic phase separated, evaporating to dryness at reduced pressure. A brown oil was obtained which was purified by column chromatography to provide 6.5 g (11%) of the desired product.

EXAMPLE 20

2-[[[3-methyl-4-(3-methoxypropoxi)-2-pyridil]methyl]sulfinyl]-1H-benzomidazol 23 g of 2-[[[3-methyl-4-(3-methoxypropoxi)-2-pyridil]methyl]thio]-1H-benzomidazol were dissolved in 11.5 ml of methanol and 90 mg of ammonium molybdate were added. The solution was cooled to 5° C., adding 0.87 g of sodium percarbonate, keeping stirred at the same temperature for 6 h. After conclusion of the reaction, 22 ml of water were added. This was heated to 20° C. and the pH of the mixture was adjusted to 7.5 with acetic acid. The mixture was extracted with 50 ml of dichloromethane and the organic phase was separated and washed with 100 ml of water. The solvent was evaporated at reduced pressure, providing 2.0 g of rabeprazol (yield: 81%).

EXAMPLE 21

2[[[4-(3-hidroxipropoxi)-3-methyl-2-pyridil]methyl]thio]-1H-benzomidazol 20.0 g of 2-[[(3-methyl-4-nitro-2-pyridil)methyl]thio]-1H-benzimidazol and 27.6 g of potassium carbonate were suspended in 60 ml of 1,3-propanodiol. The mixture was heated to 60° C. for 29 h and then cooled to 20° C. 200 ml of water, 160 ml of dichloromethane and 80 ml of methanol were added, separating the organic phase and extracting the aqueous phase with more dichloromethane. The organic extracts were joined, adding 200 ml of water and 25% sodium hydroxide to a pH 14. The organic phase was separated and extracted twice with 100 ml of water. The aqueous extracts were joined adding 10% hydrochloric acid to a pH 6.5; 150 ml of dichloromethane and 150 ml of methanol were added, separating the organic phase and evaporating to dryness at reduced pressure to provide 6.41 g (29%) of the desired product.

EXAMPLE 22

2-[[[4-(3-hidroxipropoxi)-3-methyl-2-pyridil]methyl]sulfinyl]-1H-benzomidazol 2.2 g of 2-[[[4-(3-hydroxipropoxi)-3-methyl-2-pyridil]methyl]thio]-1H-benzomidazol were dissolved in 11.5 ml of methanol and 90 mg of ammonium molybdate were added. The solution was cooled to 5° C., adding 0.87 g of sodium percarbonate and kept stirred at the same temperature for 6 h. After conclusion of the reaction, 22 ml of water were added. This was heated to 20° C. and the pH of the mixture was adjusted to 7.5 with acetic acid. The mixture was extracted with 150 ml of dichloromethane and the organic phase separated. The solvent was evaporated at reduced pressure, providing 2.0 g (86%) of the desired product.

What is claimed is:

1. A method for obtaining derivatives of [[(pyridil substituted)methyl]thio]benzimidazole having formula (I)

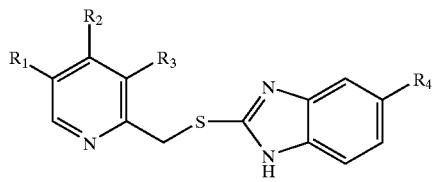

(I)

wherein,
each of $R_1$, $R_3$ and $R_4$, independently of each other, is selected from the group consisting of a hydrogen, an alkyl group with 1 to 6 carbon atoms, an alkoxy group with 1 to 6 carbon atoms, and a fluorinated alkoxy group with 1 to 6 carbon atoms; and $R_2$ is selected from the group consisting of a nitro group, a halogen, an alkoxy group with 1 to 6 carbon atoms, a halogenated alkoxy group with 1 to 6 carbon atoms, and —O—$(CH_2)_n$—$OR_8$, wherein n is an integer from 1 to 6, and $R_8$ represents hydrogen or an alkyl group with 1 to 6 carbon atoms, said method comprising:

a) reacting an N-oxide of methylpyridine with a compound having formula (IV)

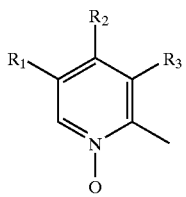

(IV)

wherein $R_1$, $R_2$ and $R_3$ are as described previously with:

(i) an anhydride of an activated carboxylic acid having formula $(R_6CO)_2O$, wherein $R_6$ is a halogenated alkyl group; or (ii) an anhydride of sulfonic acid having formula $(R_7SO_2)_2O$, wherein $R_7$ is selected from the group consisting of an alkyl group, a halogenated alkyl group, and an aryl group optionally substituted with an alkyl group, said reaction being carried out in an organic solvent to provide an intermediate with formula (V) or its corresponding salt

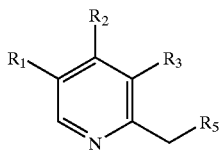

(V)

wherein $R_1$, $R_2$ and $R_3$ are as described previously; and $R_5$ is $OCOR_6$ or $OSO_2R_7$ wherein $R_6$ and $R_7$ are as described previously; and b) reacting said intermediate having formula (V) with a derivative of 2-mercaptobenzimidazole having formula (III)

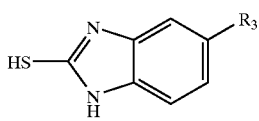

(III)

wherein $R_4$ is as defined above, in the presence of a base, in an organic solvent, to provide the compound with formula (I).

2. The method of claim 1, wherein the organic solvent used in step (a) is a chlorinated solvent or an ether.

3. The method of claim 2, wherein said organic solvent used in step (a) is selected from the group consisting of dichloromethane, 1,2-dichloroethane, chloroform and 1,1,1-trichloroethane.

4. The method of claim 1, wherein step (a) is carried out at a temperature between about 20° C. and 90° C.

5. The method of claim 4, wherein step (a) is carried out at a temperature between about 60° C. and 84° C.

6. The method of claim 1, wherein said activated carboxylic acid anhydride is trifluoroacetic anhydride.

7. The method of claim 1, wherein said anhydride of sulfonic acid is methansulfonic anhydride or toluensulfonic anhydride.

8. The method of claim 1, wherein said organic solvent used in step (b) is selected from the group consisting of a chlorinated solvent, an ether, and an alcohol.

9. The method of claim 8, wherein organic solvent used in step (b) is selected from the group consisting of dichloromethane, 1,2-dichloroethane, chloroform, 1,1,1-trichloroethane or methanol.

10. The method of claim 1, wherein said intermediate having formula (V) is reacted, in the same reaction medium used for step (a), with the derivative of 2-mercaptobenzimidazole with the formula (III).

11. The method of claim 1, wherein said intermediate with the formula (V), or its corresponding salt, is isolated before reacting it with the derivative of 2-mercaptobenzimidazole with the formula (III).

12. The method of claim 1, wherein step (b) takes place at a temperature between about 10° C. and 40° C.

13. The method of claim 1, wherein said base is triethylamine or sodium methoxide.

14. The method of claim 1, wherein said compound with the formula (I) is isolated as a solid by precipitation in water/alcohol or water/acetone.

15. The method of claim 1, further comprising oxidizing a thioether group present in the derivative of [[(pyridil substituted)methyl]thio]benzimidazole having the formula (I), thereby enhancing therapeutic activity.

16. The method of claim 15, wherein $R_2$ of formula (I) is a nitro group or a halogen and wherein said method further comprises before performing the oxidation of the thio group substituting said nitro group or halogen with the corresponding alkoxy group to provide a compound with formula (I), wherein $R_2$ is selected from the group consisting of an alkoxy group with 1 to 6 carbon atoms, a halogenated alkoxy group with 1 to 6 carbon atoms, and —O—$(CH_2)_n$—$OR_8$, wherein n is an integer from 1 to 6, and $R_8$ represents hydrogen or an alkyl group with 1 to 6 carbon atoms.

17. A compound having formula (V) and its corresponding salts

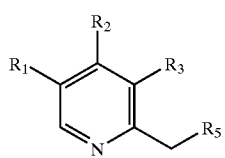

(V)

wherein:

each of $R_1$ and $R_3$, independently of each other, is selected from the group consisting of hydrogen, an alkyl group with 1 to 6 carbon atoms, and an alkoxy group with 1 to 6 carbon atoms;

$R_2$ is selected from the group consisting of a nitro group, a halogen, an alkoxy group with 1 to 6 carbon atoms, a halogenated alkoxy group with 1 to 6 carbon atoms, and —O—$(CH_2)_n$—$OR_8$, wherein n is an integer from 1 and 6, and $R_8$ represents hydrogen or an alkyl group with 1 to 6 carbon atoms; and $R_5$ is $OSO_2R_7$, wherein $R_7$ is selected from the group consisting of an alkyl group, a halogenated alkyl group and an aryl group optionally substituted with an alkyl group.

18. The compound of claim 17, wherein $R_1$ is hydrogen or methyl, $R_2$ is selected from the group consisting of nitro, chloro, methoxy, 2,2,2-trifluoroethoxy, 3-methoxypropoxy, 3-hydroxipropoxy and 3-chloropropoxy, $R_3$ is methyl or methoxy, and $R_5$ is selected from the group consisting of mesiloxy, and tosiloxy.

19. The compound of claim 17, wherein $R_1$ is hydrogen, $R_2$ is nitro, $R_3$ is methyl and $R_5$ is selected from the group consisting of trifluoroacetyloxy, mesiloxy, and tosiloxy.

20. The compound of claim 17, wherein $R_1$ is methyl, $R_2$ is nitro, $R_3$ is methyl and $R_5$ is selected from the group consisting of trifluoroacetyloxy, mesiloxy, and tosiloxy.

21. The compound of claim 17, wherein $R_1$ is hydrogen, $R_2$ is nitro or chloro, $R_3$ is methoxy and $R_5$ is selected from the group consisting of trifluoroacetyloxy, mesiloxy, and tosiloxy.

22. A method for obtaining the compound of claim 17 comprising reacting an N-oxide of methylpyridine having formula (IV)

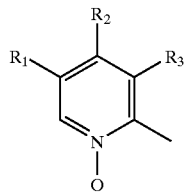

(IV)

wherein:

each of $R_1$ and $R_3$, independently of each other, is selected from the group consisting of hydrogen, an alkyl group with 1 to 6 carbon atoms, and an alkoxy group with 1 to 6 carbon atoms; and $R_2$ is selected from the group consisting of a nitro group, a halogen, an alkoxy group with 1 to 6 carbon atoms, a halogenated alkoxy group with 1 to 6 carbon atoms, and —O—$(CH_2)_n$—$OR_8$, wherein n is an integer from 1 to 6, and $R_8$ represents hydrogen or an alkyl group with 1 to 6 carbon atoms;

with:

(i) an anhydride of activated carboxylic acid having formula $(R_6CO)_2O$, wherein $R_6$ is a halogenated alkyl group, or (ii) an anhydride of sulfonic acid having formula $(R_7SO_2)_2O$, wherein $R_7$ is selected from the group consisting of an alkyl group, a halogenated alkyl group, and an aryl group, optionally substituted with an alkyl group, said reaction being carried out in an organic solvent.

* * * * *

UNITED STATES PATENT AND TRADEMARK OFFICE
CERTIFICATE OF CORRECTION

PATENT NO. : 6,723,852 B2
DATED : April 20, 2004
INVENTOR(S) : Ramon Berenguer Maimo et al.

It is certified that error appears in the above-identified patent and that said Letters Patent is hereby corrected as shown below:

Title page,
Item [54], Title, should read

-- [54] METHOD FOR OBTAINING DERIVATIVES OF [[(PYRIDYL SUBSTITTUTED)METHYL]THIO]BENZIMIDAZOLE --

Item [75], Inventors, should read:

-- [75] Inventors: Ramon Berenguer Maimo, Barcelona, Spain
  Laura Coppi, Barcelona, Spain --

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,723,852 B2 |
| APPLICATION NO. | : 10/204604 |
| DATED | : April 20, 2004 |
| INVENTOR(S) | : Ramon Berenguer Maimo et al. |

It is certified that error appears in the above-identified patent and that said Letters Patent is hereby corrected as shown below:

In the claims:

In claim 1, at column 11, lines 8-9, replace

"a) reacting an N-oxide of methylpyridine with a compound having formula (IV)"

with

-- a) reacting an N-oxide of methylpyridine with the general formula (IV) --

Signed and Sealed this

Nineteenth Day of December, 2006

JON W. DUDAS
*Director of the United States Patent and Trademark Office*